(12) United States Patent
Ruf et al.

(10) Patent No.: US 12,661,030 B2
(45) Date of Patent: Jun. 23, 2026

(54) MAGNETIC RESONANCE APPARATUS HAVING A PATIENT COMMUNICATION UNIT

(71) Applicant: Siemens Healthineers AG, Forchheim (DE)

(72) Inventors: Marcel Ruf, Langensendelbach (DE); Harald Karl, Fürth (DE)

(73) Assignee: Siemens Healthineers AG, Forchheim (DE)

( * ) Notice: Subject to any disclaimer, the term of this patent is extended or adjusted under 35 U.S.C. 154(b) by 0 days.

(21) Appl. No.: 18/641,924

(22) Filed: Apr. 22, 2024

(65) Prior Publication Data

US 2024/0350026 A1     Oct. 24, 2024

(30) Foreign Application Priority Data

Apr. 24, 2023     (EP) .................................... 23169447

(51) Int. Cl.
　　*A61B 5/055*　　　(2006.01)
　　*A61B 5/00*　　　(2006.01)
(52) U.S. Cl.
　　CPC .............. *A61B 5/055* (2013.01); *A61B 5/704* (2013.01)
(58) Field of Classification Search
　　CPC ........ A61B 5/055; A61B 5/704; G01R 33/283
　　See application file for complete search history.

(56) References Cited

U.S. PATENT DOCUMENTS

| | | | |
|---|---|---|---|
| 2006/0079763 A1 | 4/2006 | Jeung et al. | |
| 2013/0162510 A1 | 6/2013 | Ohgishi et al. | |
| 2015/0085261 A1* | 3/2015 | Lee .................... | G03B 21/2053 |
| | | | 324/318 |
| 2017/0285844 A1* | 10/2017 | Park ...................... | G06F 1/1647 |
| 2019/0170836 A1 | 6/2019 | Moore et al. | |
| 2020/0103479 A1* | 4/2020 | Bollenbeck .......... | G01R 33/385 |
| 2023/0022887 A1* | 1/2023 | Bollenbeck .......... | A61B 5/7445 |
| 2023/0144829 A1* | 5/2023 | Wan ...................... | G16H 50/20 |
| | | | 382/128 |

FOREIGN PATENT DOCUMENTS

DE     102018216644 A1     4/2020

OTHER PUBLICATIONS

Siemens AG, "Method for Indicating the Progress During an MRT Scan Procedure", 2018.
Seregin P. et al.: "Energy Harvesting Coil for Circularly Polarized Fields in Magnetic Resonance Imaging", arXiv:2106.06886v1 [physics. app-ph] Jun. 13, 2021 https://www.semanticscholar.org/paper/Energy-Harvesting-Coil-for-Circularly-Polarized-in-Seregin-Burmistrov/fca308df0eb861a2e25b56e4c29a0f168cbc2b00/figure/0.
Ganti A. et al.: "A Novel Energy Harvesting Circuit for RF Surface Coils in the MRI System", IEEE Trans Biomed Circuits Syst. Aug. 2021; 15(4):791-801 https://pubmed.ncbi.nlm.nih.gov/34383652/.

* cited by examiner

*Primary Examiner* — Alexei Bykhovski
(74) *Attorney, Agent, or Firm* — Banner & Witcoff, Ltd.

(57)　　　ABSTRACT

A magnetic resonance apparatus having a magnet unit, a patient-receiving region that is at least in part surrounded by the magnet unit and is designed to receive a patient for a magnetic resonance examination, and a patient communication unit that includes a display unit having an e-paper display arranged within the patient-receiving region.

8 Claims, 2 Drawing Sheets

MAGNETIC RESONANCE APPARATUS HAVING A PATIENT COMMUNICATION UNIT

TECHNICAL FIELD

The aspects of the present disclosure relate to a magnetic resonance apparatus having a magnet unit, a patient-receiving region that is at least in part surrounded by the magnet unit, wherein the patient-receiving region is designed so as to receive a patient for a magnetic resonance examination, and a patient communication unit.

BACKGROUND

Independent of the grammatical term usage, individuals with male, female, or other gender identities are included within the term.

During a magnetic resonance examination, the patient is located within an examination space within which the magnetic resonance apparatus is arranged. The patient is positioned within the patient-receiving region for the magnetic resonance examination. On the other hand, a medical operating personnel who is supervising the magnetic resonance examination, for example, a doctor, is in a control space during the magnetic resonance examination. From this control space, the medical operating personnel can control and monitor the magnetic resonance examination.

For communication with the patient during the magnetic resonance examination, the magnetic resonance apparatus usually has a patient communication unit. The patient communication unit is used to convey information and/or instructions to the patient during the magnetic resonance examination. For example, breathing instructions that are required for the magnetic resonance examination can be conveyed to the patient, such as, in particular, breathing hold instructions and/or breathhold signals that tell the patient when to hold their breath. This is especially important for thoracic examinations. In addition, the remaining scan duration and/or remaining examination time can also be communicated to the patient by means of the patient communication unit.

Up to now, such information and/or instructions have been conveyed to the patient by means of an acoustic output unit, for example, in the form of headphones that the patient wears during the magnetic resonance examination.

In contrast, an arrangement of a conventional display and/or a monitor within the patient-receiving region of a magnetic resonance apparatus has many difficulties. Thus, in particular, the magnetic resonance examination can be disrupted by interference signals from the electronics of the display, which can lead to undesired artifacts in the acquired image data and/or measurement repetitions. Furthermore, the display is positioned within a particularly strong magnetic field, for example, 1.5 T or 3 T, which can also lead to disruption of the electronics of the display itself and thus to a disruption in patient communication. A disruption of patient communication can, in turn, have a negative effect on the patient, so that individual measurements of the magnetic resonance examination may also have to be repeated. Another difficulty in attaching a conventional display is the power supply to the display, which in turn can lead to disruption of the magnetic resonance examination.

SUMMARY

An object in accordance with aspects of the present disclosure is, in particular, to provide visual patient communication in a simple manner during a magnetic resonance examination on a patient. The object is achieved by the features of the claims.

The aspects of the disclosure relate to a magnetic resonance apparatus having a magnet unit, a patient-receiving region that is at least in part surrounded by the magnet unit, wherein the patient-receiving region is designed so as to receive a patient for a magnetic resonance examination, and a patient communication unit. In accordance with the aspects of the disclosure, the patient communication unit comprises a display unit having an e-paper display.

The magnetic resonance apparatus preferably comprises a medical and/or diagnostic magnetic resonance apparatus that is designed and/or configured so as to acquire medical and/or diagnostic image data, in particular medical and/or diagnostic magnetic resonance image data, of a patient. In addition, the magnetic resonance apparatus, in accordance with the aspects of the disclosure, can also be integrated into a combined magnetic resonance PET system together with a PET apparatus (positron emission tomography apparatus).

The magnetic resonance apparatus preferably comprises the magnet unit for acquiring the medical and/or diagnostic image data. In this case, the magnet unit comprises a main magnet, a gradient coil unit, and a radio frequency antenna unit. The radio frequency antenna unit, in this case, is typically arranged within the magnet unit.

The main magnet is designed so as to generate a homogeneous main magnetic field having a defined magnetic field strength, such as, for example a magnetic field strength of 0.55 T or 1.5 T or 3 T or 7 T, etc. In particular, the main magnet is designed so as to generate a strong, constant, and homogeneous main magnetic field. The gradient system is designed so as to generate magnetic field gradients that are used for spatial encoding during imaging. The radio frequency antenna unit is designed so as to emit radio frequency pulses and/or excitation pulses for generating magnetic resonance signals.

For a magnetic resonance examination, the patient, in particular the region of the patient to be examined, is positioned within the patient-receiving region of the magnetic resonance apparatus. The field of view (FOV) and/or an isocenter of the magnetic resonance apparatus are preferably arranged within the patient-receiving region. The FOV preferably comprises an acquisition region of the magnetic resonance apparatus, within which the conditions for acquiring medical image data, in particular magnetic resonance image data, are present within the patient-receiving region, such as, for example, a homogeneous main magnetic field. The isocenter of the magnetic resonance apparatus preferably comprises the region and/or point within the magnetic resonance apparatus that has the optimum and/or ideal conditions for acquiring medical image data, in particular, magnetic resonance image data. In particular, the isocenter comprises the most homogeneous magnetic field region within the magnetic resonance apparatus.

For introducing and/or positioning the patient, in particular, the region of the patient to be examined, within the patient-receiving region, the magnetic resonance apparatus comprises a patient positioning apparatus. The patient positioning apparatus has a patient table, wherein the patient table is designed so as to be movable relative to the magnet unit. In this case, the patient table is preferably designed so as to be movable in the longitudinal direction of the patient table and/or in the longitudinal direction of the patient-receiving region within the patient-receiving region in order to position the patient in an examination position within the patient-receiving region.

The patient communication unit is designed so as to communicate between a user, in particular the operating personnel who is supervising the magnetic resonance examination, and the patient during a magnetic resonance examination. For this purpose, the patient communication unit has a display unit on the patient side, which is arranged within an examination space that comprises the magnet unit. In addition, the patient communication unit can comprise a second communication unit which is arranged on the user side, in particular within a control space from which the magnetic resonance examination is controlled and/or monitored by a medical operating personnel. For example, the second communication unit can comprise an input unit for inputting information and/or instructions that are to be conveyed to the patient.

By means of the display unit, instructions and/or information, in particular examination-relevant instructions and/or information, are to be conveyed and/or communicated to the patient during the magnetic resonance examination. For example, the remaining examination time can be communicated to the patient in this manner.

The display unit comprises an e-paper display and/or an E-ink display. An e-paper display and/or E-ink display has the property that it reflects light like normal paper. In particular, an e-paper display and/or E-ink display has the property that it comprises a passive display, in particular, a non-illuminated display. An e-paper display and/or an E-ink display can also be referred to as a reflective display.

The display unit is preferably arranged within the examination space in such a manner that a patient in an examination position has a direct view of the display unit, in particular of the e-paper display and/or the E-ink display. In this case, the display unit can be arranged on the housing that surrounds the patient-receiving region or on the patient table.

Such displays, in particular e-paper displays and/or E-ink displays, have the advantage that displayed information and/or instructions can be displayed and/or shown permanently without a power supply. In particular, such displays, in particular e-paper displays and/or E-ink displays, only require energy in the event of a change in a display content and/or presentation content. Hence, the required energy is particularly low. For example, an e-paper display and/or E-ink display requires a current in the range of a few 100 mA. In particular, this advantageously makes it possible to omit constantly energized electronics of the display unit during a magnetic resonance examination. In particular, an energy requirement can be kept particularly low in this manner. Thus, an undesired interaction between the display unit and the magnet unit during a magnetic resonance examination can also be kept low and/or prevented. For example, the display unit can be designed to change the display content of the e-paper display and/or E-ink display only in measurement pauses, in particular in pauses between two radio frequency pulses to be played. In particular, such undesired disruptions of the display unit and/or the magnetic resonance data acquisition can be reduced and/or prevented. In this manner, it is possible to provide visual information to the patient during the magnetic resonance examination in a structurally simple manner.

In addition, such display units, in particular the e-paper display and/or the E-ink display, can be designed in a particularly compact and space-saving manner. In particular, a lounge area that is available to the patient within the patient-receiving region can be maintained in this manner by an arrangement of the display unit within the patient-receiving region.

In one advantageous development of the magnetic resonance apparatus in accordance with the aspects of the disclosure, it is possible to provide that the display unit has an antenna element, wherein the antenna element is designed so as to extract energy during a magnetic resonance examination. The antenna element is preferably designed so as to receive electromagnetic waves, wherein energy, in particular electrical energy, is extracted from the electromagnetic waves that are received. In particular, the display unit and thus also the antenna element are arranged within the patient-receiving region during a magnetic resonance examination, wherein the antenna element is preferably designed so as to receive radio frequency pulses of the magnet unit in order to extract energy.

This aspect of the disclosure has the advantage that the display unit can be operated autonomously during a magnetic resonance examination within the patient-receiving region. In particular, this advantageously makes it possible to omit an additional power supply to the display unit, for example, by means of additional power cables and/or by means of batteries. In particular, the display unit can be operated in this manner in a wireless and/or cable-free manner. A further advantage is that it is also possible to omit monitoring the state of charge of batteries. Thus, the display unit is always ready for use within the patient-receiving region. In addition, it is thus possible to provide a flexible positioning of the display unit, which can be adapted to a patient's positioning.

In one advantageous development of the magnetic resonance apparatus in accordance with the aspects of the disclosure, it is possible to provide that the antenna element is adapted to a transmission frequency of a radio frequency antenna unit of the magnet unit, in particular during a magnetic resonance examination. In this manner, energy can be extracted in a structurally simple manner and, in addition, an external energy supply can be omitted. Furthermore, electrical energy is always available to the display unit, in particular the e-paper display and/or the E-ink display, during a magnetic resonance examination. In addition, disruptions of the display unit, in particular the e-paper display and/or E-ink display, can be prevented during a magnetic resonance examination.

In one advantageous development of the magnetic resonance apparatus in accordance with the aspects of the disclosure, it is possible to provide that the display unit has an energy storage element. The energy storage element preferably comprises rechargeable batteries, such as capacitors, for example. This aspect of the disclosure has the advantage that electrical energy, in particular energy that is extracted by means of the antenna element, can be stored for use by the display unit. In particular, electrical energy can also be available for the display unit, the e-paper display, and/or the E-ink display, even if the magnetic resonance examination has not yet been started, such as, for example, after the patient has been introduced into the patient-receiving region. In particular, the aspect of the display unit having the energy storage element has the advantage that it is possible to provide a constant current and/or a constant voltage for the operation of the display unit. In addition, voltage peaks that occur during energy extraction are not transmitted directly to an electronic system of the display unit, but rather a smoothing effect occurs due to the energy storage element, in particular the capacitors.

In one advantageous development of the magnetic resonance apparatus in accordance with the aspects of the disclosure, it is possible to provide that the display unit comprises a first radio module that is designed so as to receive control data. The first radio module preferably comprises a radio interface that is designed so as to receive radio data, in particular control data. Preferably, a display on the e-paper display and/or the E-ink display is controlled by means of the control data. For example, the control data can contain information to be displayed, which is displayed on the e-paper display and/or E-ink display. In addition, the control data can also trigger a display of information to be displayed on the e-paper display and/or E-ink display, wherein the information to be displayed is already stored on the display unit. For this purpose, the radio module preferably corresponds to a second radio module that transmits the control data to the first radio module. The second radio module is preferably located outside the patient-receiving region. The two radio modules preferably communicate at a frequency that is outside a transmission spectrum and/or a reception spectrum of the magnetic resonance apparatus.

This aspect of the disclosure has the advantage that simple data transmission from a control space and/or from a user to the patient can take place. In addition, the data can be transmitted to the display unit in this manner in a wireless and/or cable-free manner, and an additional data line can advantageously be omitted.

In one advantageous development of the magnetic resonance apparatus in accordance with the aspects of the disclosure, it is possible to provide that the patient communication unit has a control unit and a second radio module, wherein the second radio module is designed for data transmission with the first radio module, wherein the control unit together with the second radio module is arranged outside the patient-receiving region.

The control unit is preferably designed so as to generate control signals that are to be transmitted to the first radio module and, thus, to the display unit. The control unit comprises at least one computing module and/or a processor. In particular, the control unit is designed so as to execute computer-readable instructions. In particular, the control unit can comprise a storage unit, wherein computer-readable information is stored on the storage unit, wherein the control unit is configured so as to load the computer-readable information from the storage unit and so as to execute the computer-readable information in order to control data transmission between the two radio modules and/or in order to generate control data for controlling a display on the display unit.

For the most part, the components of the control unit can be designed in the form of software components. In principle, however, some of these components can also be implemented in the form of software-supported hardware components, for example FPGAs or the like, in particular when particularly rapid calculations are involved. The required interfaces can likewise be designed as software interfaces, for example, if it is only a matter of transferring data from other software components. However, they can also be designed as interfaces that are designed in terms of hardware and are controlled by suitable software. It is, of course, also conceivable for a plurality of the aforementioned components to be implemented in the form of a single software component or software-supported hardware component in a combined manner.

Here, too, the advantage can be achieved that simple data transmission, in particular a cable-free and/or wireless data transmission, from a control space and/or from the user to the patient can take place.

In one advantageous development of the magnetic resonance apparatus in accordance with the aspects of the disclosure, the display unit comprises a circuit board having an electronic module, wherein the first radio module is arranged on the circuit board. The circuit board is preferably connected to the e-paper display and/or E-ink display for data transmission and/or energy transmission. In this manner, it is possible to achieve a particularly compact and space-saving arrangement of the first radio module within the display unit.

In one advantageous development of the magnetic resonance apparatus in accordance with the aspects of the disclosure, it is possible to provide that the magnet unit has a housing that surrounds the patient-receiving region, and the display unit is arranged on the housing. The housing that surrounds the patient-receiving region comprises, for example, a support tube on which the radio frequency antenna unit is arranged on a side that is remote from the patient-receiving region. In this case, the display unit is preferably arranged on a surface of the housing that surrounds the patient-receiving region that is opposite a positioning surface for positioning the patient. The aspects of the disclosure make it possible to achieve direct visibility of the e-paper display and/or E-ink display for the patient.

In one advantageous development of the magnetic resonance apparatus in accordance with the aspects of the disclosure, it is possible to provide that the display unit has at least one fastening element, wherein the at least one fastening element is designed so as to be fastened in a detachable manner between the display unit and the housing that surrounds the patient-receiving region. In this manner, a position of the display unit can advantageously be adapted to a position of the patient, in particular to an examination position of the patient. In particular, the display unit can be arranged at different positions on the housing that surrounds the patient-receiving region.

The at least one fastening element can be designed, for example, so as to adhere the display unit to the housing that surrounds the patient-receiving region. In this case, the at least one fastening element can be designed, for example, as a double-sided adhesive tape. In addition, defined positions on the housing that surrounds the patient-receiving region can also be provided with a fastening element that allows the display unit to be latched and/or suspended and/or clamped on the housing that surrounds the patient-receiving region. Depending on the examination position of the patient, the display unit can be fastened to one of these positions.

In one advantageous development of the magnetic resonance apparatus in accordance with the aspects of the disclosure, it is possible to provide that the magnetic resonance apparatus comprises a patient table having at least one removable fastening element, wherein the at least one fastening element can be fastened to the patient table in such a manner that the display unit is arranged in a field of view of the patient when arranged and/or fastened on the fastening element. In particular, the e-paper display and/or E-ink display are arranged in the field of view of the patient. For example, the at least one fastening element can comprise an arcuate holding element that can be fastened to the patient table, in particular in the vicinity of the head of the patient on the patient table, so that the display unit can be positioned and/or arranged in the field of view of the patient. In this case, the display unit can preferably be introduced into the patient-receiving region together with the patient table. In this manner, the display unit is always in the field of view of the patient, regardless of its position within the patient-receiving region. In particular, it is possible in this manner to achieve unimpaired visibility of the e-paper display and/or E-ink display for the patient.

BRIEF DESCRIPTION OF THE DRAWINGS

Further advantages, features, and details of the aspects of the disclosure are evident in the following described exemplary aspects and also with the aid of the drawings.

In the drawings.

DETAILED DESCRIPTION

Figure 1:
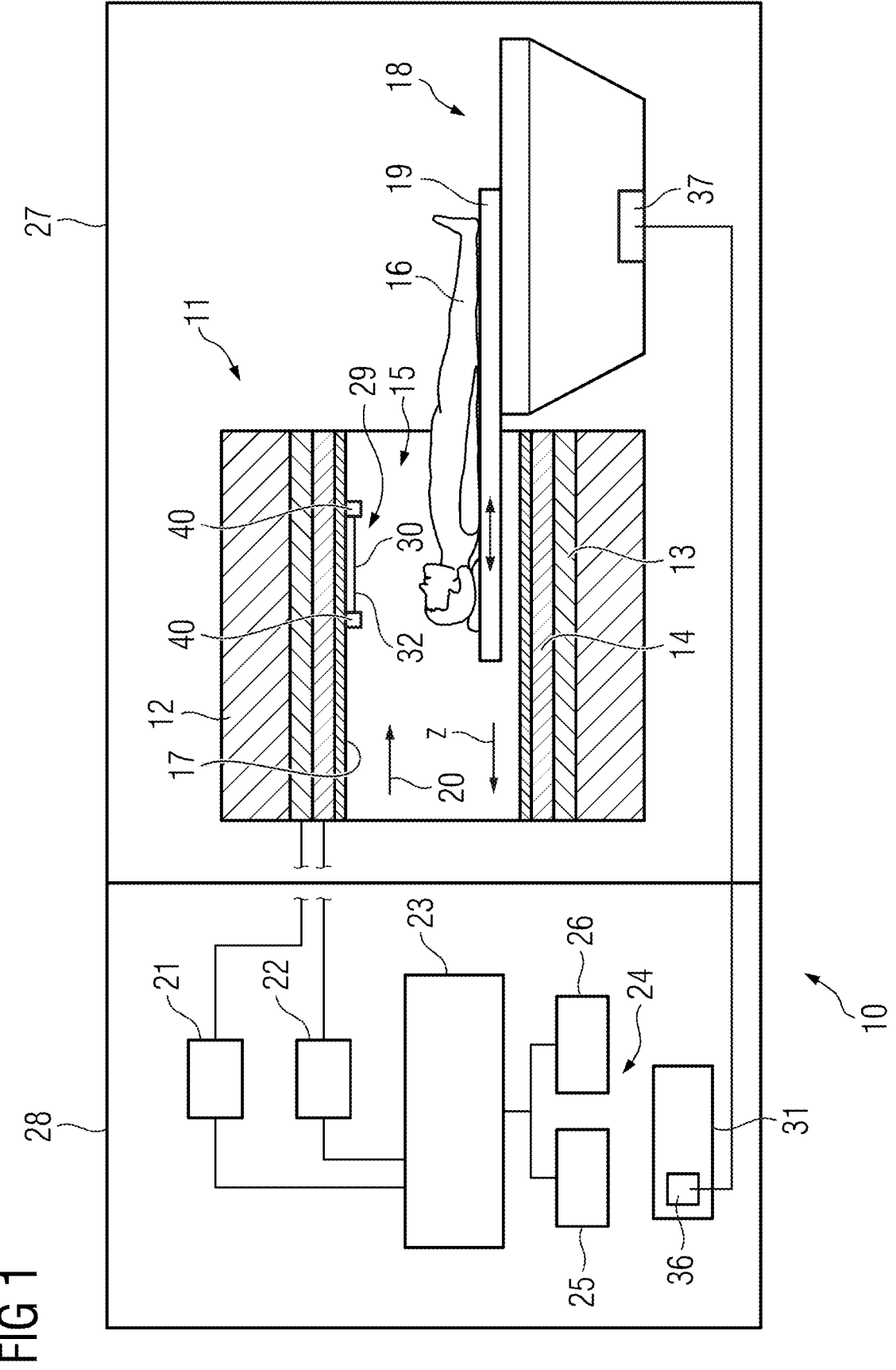
FIG. 1 shows a magnetic resonance apparatus in accordance with the aspects of the disclosure having a patient communication unit in a schematic illustration.

FIG. 1 illustrates schematically a magnetic resonance apparatus 10. The magnetic resonance apparatus 10 comprises a magnet unit 11 having a main magnet 12, a gradient coil unit 13 and a radio frequency antenna unit 14. In addition, the magnetic resonance apparatus 10 has a patient-receiving region 15 for receiving a patient 16. In the present exemplary aspect, the patient-receiving region 15 is designed in the form of a cylinder and is surrounded in a circumferential direction by the magnet unit 11 in the form of a cylinder. In principle, however, a design of the patient-receiving region 15 deviating therefrom is conceivable at any time. The magnet unit 11 also has a housing 17 that surrounds the patient-receiving region 15. The housing 17 that surrounds the patient-receiving region 15 preferably comprises a support tube that surrounds the patient-receiving region 15 in the form of a cylinder. The radio frequency antenna unit 14 of the magnet unit 11 is preferably arranged on a side of the support tube that is remote from the patient-receiving region 15.

The patient 16 can be pushed and/or introduced by means of a patient positioning apparatus 18 of the magnetic resonance apparatus 10 into the patient-receiving region 15. For this purpose, the patient positioning apparatus 18 has a patient table 19 that is designed to be movable within the patient-receiving region 15. In particular, in this case, the patient table 19 is mounted so as to be movable in the direction of a longitudinal extent of the patient-receiving region 15 and/or in the z-direction.

The main magnet 12 of the magnet unit 11 comprises a superconducting main magnet 12 for generating a strong and, in particular, constant main magnetic field 20. The gradient coil unit 13 of the magnet unit 11 is designed to generate magnetic field gradients that are used for spatial encoding during imaging. The gradient coil unit 13 is controlled by means of a gradient coil unit 21 of the magnetic resonance apparatus 10. The radio frequency antenna unit 14 of the magnet unit 11 is designed so as to excite a polarization that occurs in the main magnetic field 20 that is generated by the main magnet 12. The radio frequency antenna unit 14 is controlled by a radio frequency antenna control unit 22 of the magnetic resonance apparatus 10 and radiates radio frequency magnetic resonance sequences into the patient-receiving region 15 of the magnetic resonance apparatus 10.

In order to control the main magnet 12, the gradient control unit 21, and the radio frequency antenna control unit 22, the magnetic resonance apparatus 10 has a system control unit 23. The system control unit 23 centrally controls the magnetic resonance apparatus 10, such as, for example, performing a predetermined imaging gradient echo sequence. In addition, the system control unit 23 comprises an evaluation unit (not shown in more detail) for evaluating medical image data that is acquired during the magnetic resonance examination.

The magnetic resonance apparatus 10 further comprises a user interface 24 that is connected to the system control unit 23. Control information such as imaging parameters, for example, and reconstructed magnetic resonance images can be displayed on a display unit 25, for example, on at least one monitor, of the user interface 24 for a medical operating personnel. Furthermore, the user interface 24 has an input unit 26 by means of which information and/or parameters can be input by a user during a measuring procedure.

The magnet unit 11 of the magnetic resonance apparatus 10 is arranged together with the patient positioning apparatus 18 within an examination space 27. In contrast, the system control unit 23 is arranged together with the user interface 24 within a control space 28. The control space 28 is designed so as to be separate from the examination space 27. In particular, the examination space 27 is shielded from the control space 28 with regard to radio frequency radiation. During a magnetic resonance examination, the patient 16 is located within the examination space 27, while the medical operating personnel are located within the control space 28.

For communication between the operator, in particular a medical operating personnel, and the patient 16 during the magnetic resonance examination, the magnetic resonance apparatus 10 has a patient communication unit 29. By means of the patient communication unit 29, information and/or instructions, in particular examination-relevant information and/or instructions, are to be conveyed and/or communicated to the patient 16 during the magnetic resonance examination, such as, for example, a remaining examination time and/or breathing commands, etc. The patient communication unit 29 has a display unit 30, which is arranged within the examination space 27, in particular within the patient-receiving region 15 and thus in the vicinity of the patient 16. In addition, the patient communication unit 29 also has a user-side communication unit 31, which is arranged in the control space 28.

Figure 2:
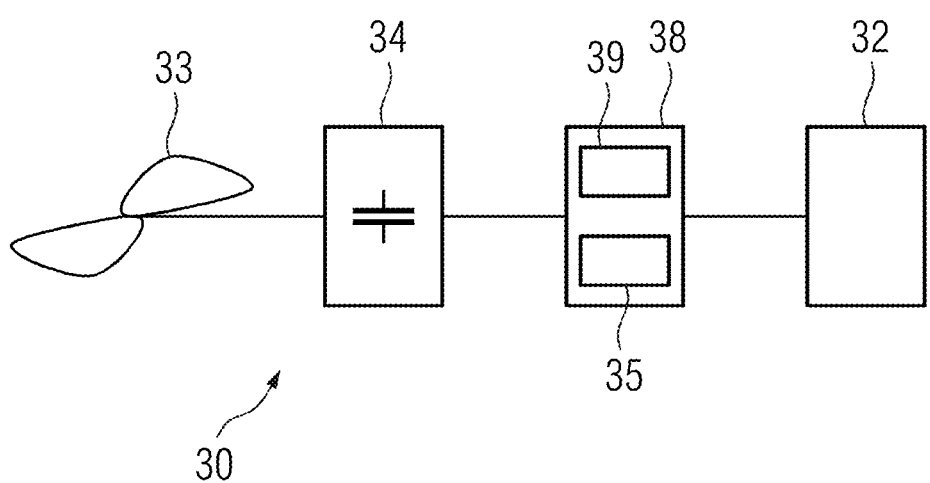
FIG. 2 shows a display unit of the patient communication unit.

The display unit 30 is illustrated in more detail in FIG. 2. The display unit 30 comprises an e-paper display 32 and/or an E-ink display, which is arranged within the patient-receiving region 15. The display unit 30 also has an antenna element 33, which is designed so as to extract energy, in particular to extract electrical energy, during a magnetic resonance examination. In particular, the antenna element 33 is designed to extract electrical energy from the electromagnetic waves and/or the electromagnetic radiation of the transmitted transmission pulses and/or radio frequency pulses of the radio frequency antenna unit 14. In this case, the antenna element 33 is preferably configured so as to be adapted to a transmission frequency of the radio frequency antenna unit 14.

The display unit 30 furthermore has an energy storage element 34. The energy storage element 34 is designed so as to store electrical energy and comprises a rechargeable battery, in which the electrical energy that is extracted from the antenna element 33 can be stored and, if required, can be output to the e-paper display 32 and/or the E-ink display and/or electronics of the display unit 30. The rechargeable battery preferably comprises capacitors for storing the electrical energy.

In addition, the display unit 30 comprises a first radio module 35 of the patient communication unit 29, said first radio module being designed so as to receive control data for controlling the e-paper display 32 and/or the E-ink display. The patient communication unit 29 also has a control unit 36 and a second radio module 37, wherein the user-side communication unit 31 includes the control unit 36 within the control space 28. In this case, the second radio module 37 is arranged within the examination space 27, for example, on a base unit of the patient positioning apparatus 18, wherein the second radio module 37 is connected to the control unit 36 by means of a data connection. The first radio module 35 and the second radio module 37 are designed so as to transmit data, in particular, so as to transmit and/or exchange control data for controlling the e-paper display 32 and/or the E-ink display between the user-side communication unit 31 and the display unit 30. A notification on the e-paper display and/or the E-ink display is controlled by means of the control data. The two radio modules 35, 37 preferably communicate at a frequency that is outside a transmission spectrum and/or a reception spectrum of the radio frequency antenna unit 14.

The display unit 30 furthermore has a circuit board 38 having an electronics module 39. Furthermore, the first radio module 35 is also arranged on the circuit board 38.

The display unit 30 is arranged on the housing 17 that surrounds the patient-receiving region 15 (FIG. 1). For this purpose, the display unit 30 has at least one fastening element 40, which is designed so as to be fastened in a detachable manner between the display unit 30 and the housing 17, in particular the support tube, that surrounds the patient-receiving region 15. For such an arrangement of the display unit 30 on the housing 17 that surrounds the patient-receiving region 15, the display unit 30 can also have two or more fastening elements 40.

In this case, the at least one fastening element 40 can comprise an adhesive element, that is designed so as to adhere the display unit 30 to the housing 17 that surrounds the patient-receiving region 15. Preferably, the adhesive element causes a detachable adhesive connection between the display unit 30 and the housing 17 that surrounds the patient-receiving region 15.

As an alternative, the housing 17 that surrounds the patient-receiving region 15 can also comprise defined receiving locations for receiving and/or arranging the display unit 30. For this purpose, the display unit 30 can preferably have a clamping element and/or a latching element for a clamping connection and/or a latching connection to the housing 17 that surrounds the patient-receiving region 15. In addition, further fastening elements that appear expedient to the person skilled in the art for fastening and/or arranging the display unit 30 on the housing 17 that surrounds the patient-receiving region 15 are conceivable at any time. In particular, the display unit 30 is also detachably arranged in the defined receiving locations, so that, depending on the examination position of the patient 16, the display unit 30 can be positioned in one of the receiving locations and the patient 16 has a direct view of the display unit 30.

Figure 3:
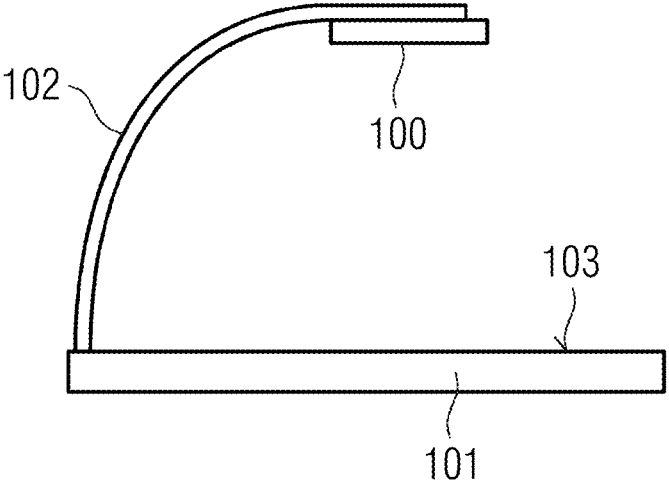
FIG. 3 shows an alternative arrangement of the display unit on a patient table.

In FIG. 3, an alternative exemplary aspect of the magnetic resonance apparatus is illustrated. In principle, essentially identical components, features, and functions are denoted by the same reference characters. The following description is essentially limited to the differences from the exemplary aspect in FIGS. 1 and 2, wherein in relation to identical components, features, and functions, reference is made to the description of the exemplary aspect in FIGS. 1 and 2.

The magnetic resonance apparatus in FIG. 3 differs from the magnetic resonance apparatus 10 in FIG. 1 in an arrangement of the display unit 100. In the present exemplary aspect, the display unit 100 is arranged on the patient table 101, wherein only the patient table 101 having the display unit 100 can be seen in a sectional illustration in FIG. 3. For this purpose, the patient table 101 has a removable fastening element 102 that extends and/or clamps in an arcuate manner over the patient table 101 in the transverse direction of the patient table 101, in particular a mounting surface 103 of the patient table 101 for mounting the patient 16. The display unit 30 is arranged removably on this fastening element 102. In this case, the display unit 30 is arranged on the fastening element 102 in such a manner that the display unit 30 is arranged directly in the field of view of the patient 16. When moving the patient table 101, for example, when moving the patient table 101 into the patient-receiving region 15, the display unit 30 is, therefore, always directly in the field of view of the patient 16.

A further aspect of the display unit 30 corresponds to the above statements of the description of FIG. 2, to which reference is hereby made.

A further aspect of the magnetic resonance apparatus also corresponds to the statements of the description of FIG. 1, to which reference is hereby made.

The illustrated magnetic resonance apparatuses 10, 100 can, of course, comprise further components that usually have magnetic resonance apparatuses 10, 100. A general function of a magnetic resonance apparatus 100 is moreover known to the person skilled in the art so a detailed description of the further components is omitted.

Although the aspects of the disclosure have been further illustrated and described in detail by the preferred exemplary aspects, the aspects of the disclosure are not limited in this regard by the disclosed examples, and other variations can be derived therefrom by the person skilled in the art without departing the scope of the aspects of the disclosure.

The invention claimed is:

1. A magnetic resonance apparatus, comprising:
a magnet unit comprising a radio frequency antenna unit;
a patient-receiving region that is at least in part surrounded by the magnet unit, and is designed to receive a patient for a magnetic resonance examination; and
a patient communication unit including a display unit having an e-paper display, wherein the display unit comprises:
a first radio module that is designed so as to receive control data, wherein the first radio module is configured to communicate at a frequency that is outside a transmission spectrum and/or a reception spectrum of the radio frequency antenna unit, and
a circuit board having an electronic module, wherein the first radio module is arranged on the circuit board, and
wherein the display unit is configured to change display content only during measurement pauses between radio frequency pulses to be played, thereby reducing or preventing disruptions to magnetic resonance data acquisition.

2. The magnetic resonance apparatus as claimed in claim 1,
wherein the display unit has an antenna element that is designed to extract energy during a magnetic resonance examination.

3. The magnetic resonance apparatus as claimed in claim 2, wherein the antenna element is adapted to a transmission frequency of the radio frequency antenna unit of the magnet unit.

4. The magnetic resonance apparatus as claimed in claim 1, wherein the display unit has an energy storage element.

5. The magnetic resonance apparatus as claimed in claim 1, wherein the patient communication unit has a control unit and a second radio module, wherein the second radio module is designed for data transmission with the first radio module, wherein the control unit having the second radio module is arranged outside the patient-receiving region.

6. The magnetic resonance apparatus as claimed in claim 1, wherein the magnet unit has a housing that surrounds the patient-receiving region and the display unit is arranged on the housing.

7. The magnetic resonance apparatus as claimed in claim 6, wherein the display unit has at least one fastening element designed to be fastened in a detachable manner between the display unit and the housing that surrounds the patient-receiving region.

8. The magnetic resonance apparatus as claimed in claim 1, further comprising:

a patient table having at least one removable fastening element that is fastenable to the patient table such that the display unit is arranged in a field of view of the patient when arranged on the fastening element.

\* \* \* \* \*